United States Patent [19]

Frenkel et al.

[11] Patent Number: 5,603,693

[45] Date of Patent: Feb. 18, 1997

[54] THREE PART DEVICE FOR THE TRANSDERMIC ADMINISTRATION OF DRUGS BY ELECTROPHORESIS OR IONTOPHORESIS

[75] Inventors: Erik J. Frenkel, Neuchâtel; Jean-Jacques Born, Morges; Konrad Schafroth, Bern, all of Switzerland

[73] Assignee: Asulab S.A., Bienne, Switzerland

[21] Appl. No.: 300,859

[22] Filed: Sep. 6, 1994

[30] Foreign Application Priority Data

Sep. 10, 1993 [FR] France .................................. 93 10897

[51] Int. Cl.⁶ ........................................ A61N 1/00
[52] U.S. Cl. .................................... 604/20; 607/149
[58] Field of Search .......................... 604/890.1, 20–21; 607/115, 149–152

[56] References Cited

U.S. PATENT DOCUMENTS

| | | | |
|---|---|---|---|
| 4,474,570 | 10/1984 | Ariura et al. | 604/20 |
| 4,640,689 | 2/1987 | Sibalis | 604/20 |
| 4,708,716 | 11/1987 | Sibalis | 604/20 |
| 4,942,883 | 7/1990 | Newman | 128/798 |
| 5,135,479 | 8/1992 | Sibalis et al. | 604/20 |
| 5,135,480 | 8/1992 | Bannon et al. | 604/20 |
| 5,320,597 | 6/1994 | Sage, Jr. et al. | 604/20 |

FOREIGN PATENT DOCUMENTS

| | | |
|---|---|---|
| 0254965 | 2/1988 | European Pat. Off. . |
| 0336543 | 10/1989 | European Pat. Off. . |
| 2239803 | 7/1991 | United Kingdom . |
| 9115261 | 10/1991 | WIPO ........................ 604/20 |

*Primary Examiner*—Mark Bockelman
*Attorney, Agent, or Firm*—Griffin, Butler Whisenhunt & Kurtossy

[57] ABSTRACT

A device in three separable modules, for the transdermic administration of drugs by electrophoresis or iontophoresis, comprises a first active module provided with at least one system of elecrodes and one drug reservoir, a second power module provided with a power supply and a third electronic module provided with an electronic circuit, control organs and a display screen, in which the power module is situated between the two other modules and comprises, in addition to the power supply formed by one or more batteries, mechanical assembly means and electrical connection or interconnection means with the two other modules means for attaching the device to the body of a patient.

16 Claims, 4 Drawing Sheets

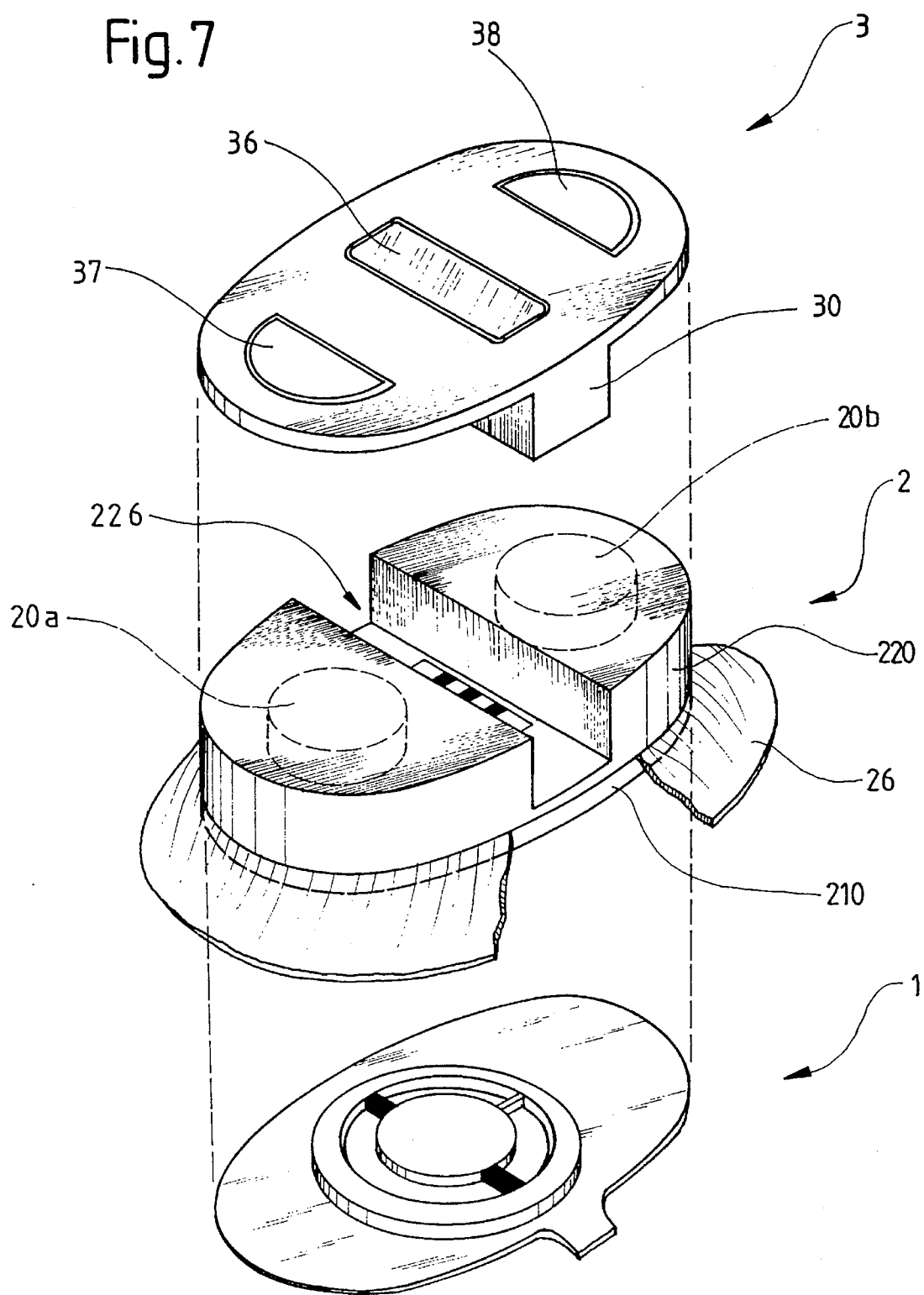

THREE PART DEVICE FOR THE TRANSDERMIC ADMINISTRATION OF DRUGS BY ELECTROPHORESIS OR IONTOPHORESIS

BACKGROUND OF THE INVENTION

The present invention concerns an device for ambulatory treatment, realized in the form of three separable modules, for the transdermic administration of drugs by electrophoresis or iontophoresis.

DESCRIPTION OF THE PRIOR ART

In addition to conventional methods of administration by oral or parenteral means, the method consisting of administering a drug by passing it through the skin barrier has been known for a long time. The drugs capable of being administered in this way can be classed into two groups. The first group consists of those drugs which pass through the skin barrier naturally by a simple application onto the skin and which pass directly into the blood stream. For such an application, the simplest device takes the form of a supporting base containing the drug to be administered, such as a gel or an impregnated pad, said supporting base being held in place by means of an adhesive tape throughout the duration of a treatment which may vary from twenty four hours to one week. Such devices, and all the improvements to which they have given rise, are generally designated by the name "passive patch". A small number of drugs already lends themselves to this mode of administration which has certain advantages, in particular at the level of a reduction in systemic toxicity. Such devices correspond for example to that disclosed in European Patent application EP 0 336 543, for the administration of, amongst others, clonidine (hypertension), or oestradiol (menopause syndrome). Despite the research carried out to facilitate or to monitor passage through the skin barrier (pH, nature of the membrane of the medium holding the drug, etc,), a large number of drugs cannot be administered by means of a passive patch, Research has thus led to the application of a technique known for almost a century, consisting of forcing passage through the skin with the aid of an electrical current which displaces the drug in the form of ions between two electrodes placed slightly apart onto the skin of the patient. When the drug in solution is already in the form of ions, the technique is referred to as electrophoresis; when the drug is carried by ions from the dilution medium, the technique is referred to as iontophoresis. Devices enabling these electrophoresis and iontophoresis techniques to be used in ambulatory treatment are generally referred to by the name of "active patches". The elementary device consists of a drug reservoir at the base of which is placed an active electrode, close to but electrically insulated from a second electrode generally called the counter-electrode, the two electrodes being connected to each other by a power supply. Contrary to traditional modes of administration by oral or parenteral means, the duration of iontopheretic or electrophoretic administration is long, which necessitates the use of a power supply having sufficient power, or more precisely which requires a choice to be made as to which should be preferred between the cumbersomeness of the power supply and its lifespan. Such a device is disclosed for example in U.S. Pat. No. 4,474,570.

It also became very quickly apparent that it was necessary to be able to check the diffusion of the drug as a function of the treatment to be applied by acting upon the power supply: the elementary model of the active patch was then completed by an integrated circuit capable of being programmed as a function of the drug administered and the treatment required to be applied to a given patient. Such an active patch consists thus of the following elements:

—a drug reservoir,
—a system of electrodes,
—a power supply, and
—an electronic circuit generally completed by a liquid crystal display.

U.S. Pat. No. 4,640,689 discloses a patch of this type. Such a device, intended to be discarded after each use, quickly showed itself to be unsatisfactory for both economical and ecological reasons. As the electronic circuit was improved, it became apparent that it was necessary to be able to maintain it. In order to avoid discarding a patch which still contains some drug but whose power supply is exhausted, or conversely, a patch with power supply remaining but whose drug reservoir is empty, it appeared necessary to be able to separate the power supply from the drug reservoir.

A device of the preceding type is disclosed for example in U.S. Pat. No. 4,708,716. According to one embodiment, the device disclosed consists of a reusable structure comprising an electronic circuit, a system of electrodes, means for attaching to the patient, as well as two casings enabling a battery and drug reservoir respectively to be put into place. According to another embodiment, the battery is applied from the exterior, on top of the patch structure. Such a device, in which the electrode system and means for attaching to the patient are preserved, does not allow one drug to be easily replaced by another, nor the same patch to be used for different patients for epidemiological reasons.

In order to avoid, at least partially, the above disadvantages, U.S. Pat. No. 5,135,479 proposes a device in which the electrode system and drug reservoir form a separable unit of the re-usable module, which is formed by the structure comprising the electronic circuit and a casing for a replaceable battery, said structure forming one piece with an attaching bracelet.

According to another device disclosed in patent application GB 2,239,803, the disposable module, comprising the electrode system and the drug reservoir, also contains a battery providing the current necessary for electrophoresis or iontophoresis. Such a device also has the disadvantages mentioned above concerning the relative exhaustion of the drug reservoir and the battery.

In all cases, as the means for attaching the patch to the patient, in particular by bracelet, forms one piece with the re-usable module, the risks of contamination remain, especially in a hospital environment, when the same patch is used by several patients.

BRIEF SUMMARY OF THE INVENTION

A purpose of the present invention is to overcome the disadvantages of the active patches known in the prior art, by providing an ambulatory treatment device for the transdermic administration of drugs by electrophoresis or iontophoresis composed of three separable modules:

—an "active module" provided at least with one electrode system and one drug reservoir,
—a "power module" provided with a supply of power necessary for electrophoresis or iontophoresis, —an electronic module provided with an electronic circuit, control organs and a display, in which the power module is situated between the two other modules and comprises, in addition to a power supply, on the one hand mechanical assembly means and electrical connection or interconnection means with the two other modules, and on the other hand means for attaching to the body of a patient.

BRIEF DESCRIPTION OF THE INVENTION

The patch according to the invention thus consists of a re-usable electronic module, and two modules in contact with the skin, which are separately disposable after a certain period of use. The patch according to the invention thus also enables prophylaxis to be improved, particularly in a hospital environment.

According to the invention, the power module contains one or several batteries, ensuring a sufficient current for an electroporetic or iontopheric therapy able to last for up to one week, whilst the drug reservoir of the active module has a capacity which can be limited to a treatment of twenty four hours, for example for reasons of therapeutic safety. The patch according to the invention thus enables the active module or the energy module to be removed selectively, according to the order in which their use expires. The need to replace the active module or the power module may be indicated on the display of the electronic module.

According to another characteristic of the invention, the worn out batteries, whatever their nature, may easily be removed from the power module and recovered to avoid polluting the environment.

The form of the patch according to the invention will generally be a function of the type of the batteries used and their arrangement in the power module, that is to say as a function of the form of the power module itself.

Generally, the power module of the patch according to the invention is comprised of two parts, a plate and a cover, realized in a rigid plastic material for example by molding or thermoforming. One of the faces of the plate is structured to keep the active module in place; the other face supports the batteries and the connection or interconnection organs between the batteries and the different modules. The cover covers totally or partially the face of the plate supporting the batteries and the connection organs. Said cover is also provided with organs enabling the electronic module to be held in place. It is evident that, without departing from the framework of the present invention, other constructions may be envisaged. It is for example possible to hold the electronic module in the patch by means of organs placed on the plate itself. Similarly, one can envisage forming the power module by the assembly of more than two parts.

The constitutive parts of the power module, including the attachment means, are assembled according to usual techniques such as adhesive bonding, welding or snap-fitting.

In the case where the patch is in the form of a circular case, and where two rod-shaped batteries are used (for example of type $R_1$), the latter can, for example, be placed flat in a V shape on the internal face of the power module plate, the circular sector which remains free being able to be used to receive the electronic module which is held in place in the power module by plugging, snap-fitting or any other appropriate means. In the case where two button-shaped batteries are used (for example of type DA63OH), the patch according to the invention will have for example the form of an oval case, the batteries being placed flat on the internal face of the power module plate, and the electronic module being adjustable on top of the cover.

Another aspect of the invention provides a patch possessing increased security of use due to the fact that the separation of the electronic module from the remaining part of the patch can be quickly effected by a simple maneuver, which enables the patch to be totally inactivated in the event that a rapid interruption of the treatment is necessary.

BRIEF DESCRIPTION OF THE DRAWINGS

The invention will be better understood with reference to the examples of embodiments illustrated by the attached drawings in which:

FIG. 7 shows a perspective view, with the three modules shown separately, of another embodiment of a patch according to the invention.

DETAILED DESCRIPTION OF THE INVENTION

Figure 1:
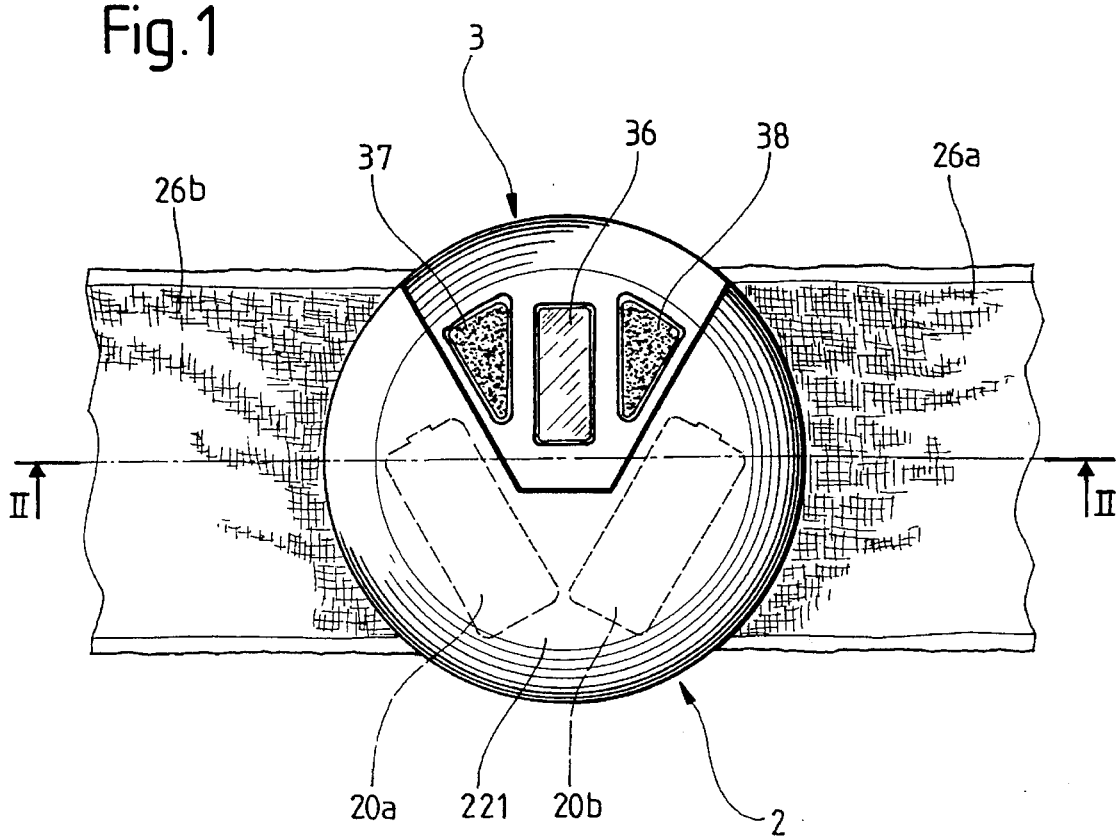
FIG. 1 shows a top view of a patch according to the invention.
Figure 2:
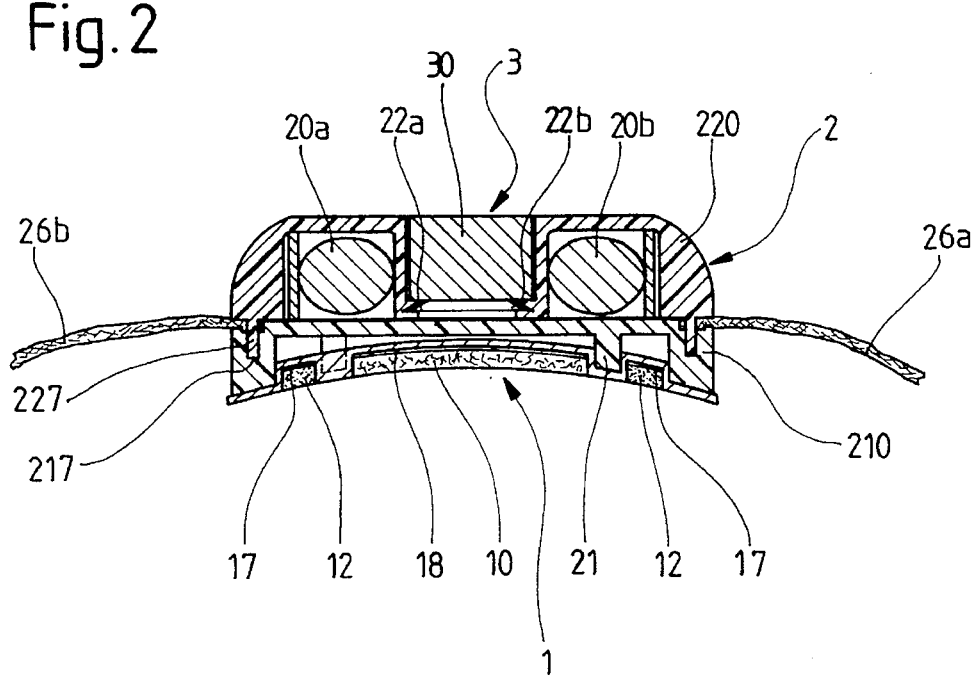
FIG. 2 shows a cross-section taken along line 2—2 of FIG. 1.
Figure 3:
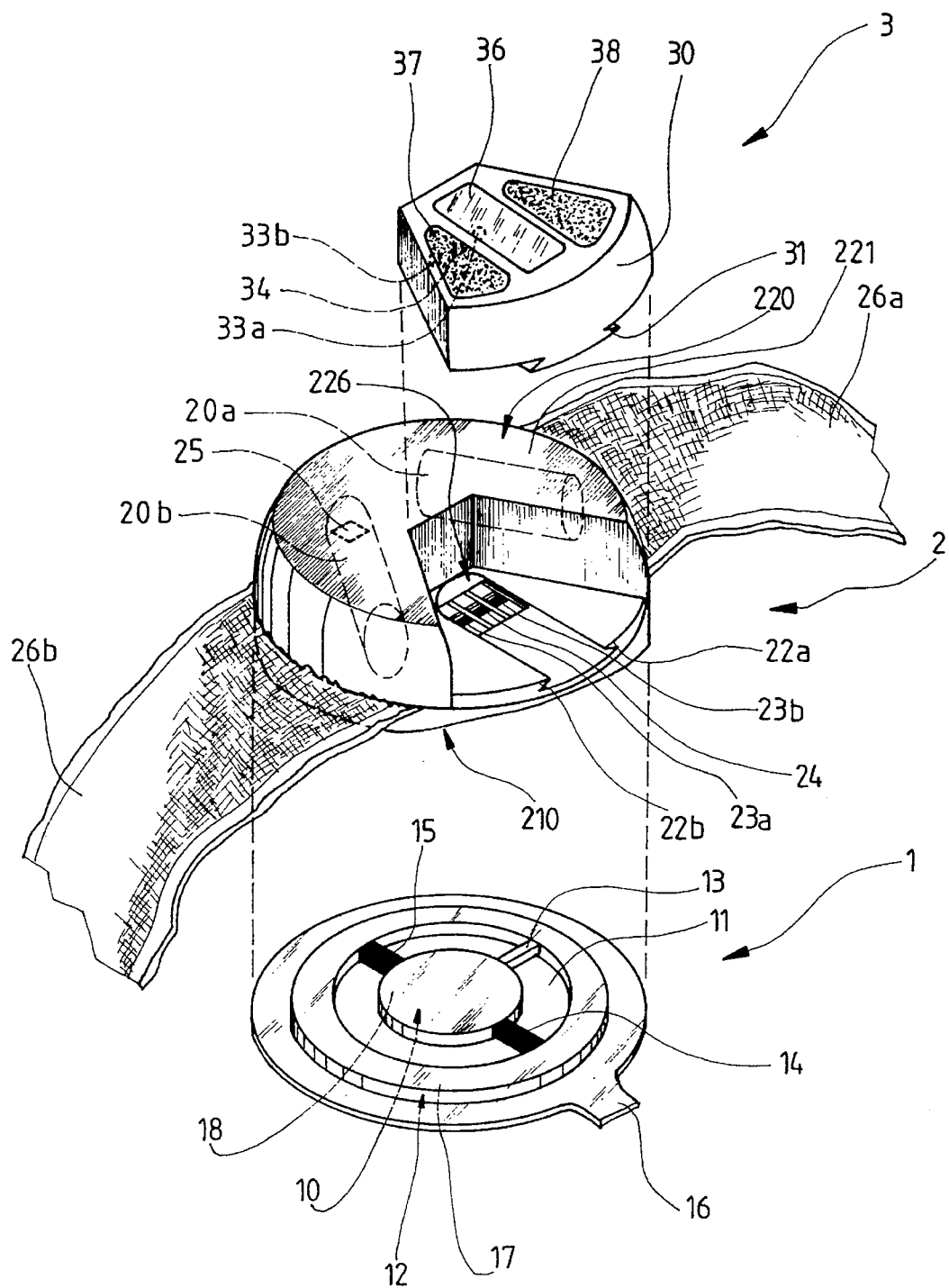
FIG. 3 shows a perspective view of the patch in FIG. 1 with the three modules shown separately.

As shown in FIGS. 1 to 3, and more particularly in FIG. 3, a patch according to the invention is formed by the assembly of three separable modules, comprising an active module 1 in contact with the patient's skin, an intermediary power module 2, and an electronic module 3 which constitutes the re-usable module.

Active module 1, of a general circular form, is formed in a flexible plastic material and comprises, on the face which is in contact with the patient's skin, a system of electrodes constituted by an active electrode 18 in the form of a disc, situated in the center and housed at the base of a reservoir 10 intended to receive the drug, and a counter-electrode 17 in the form of a ring, housed at the base of a ring-shaped reservoir 12 intended to receive a conducting gel, reservoirs 10 and 12 being separated by an insulating ring joining the opposite external edges of said reservoirs. On the opposite face, namely that which is applied onto the remaining part of the patch, reservoirs 10 and 12 delimit, in a complementary way, a groove 11 intended, on the one hand to keep active module 1 mechanically in place on the remaining part of the patch by locking into the complementary organs of the latter, and on the other hand to receive contacts 14, 15 respectively connected to electrodes 17, 18 to ensure the electrical connection of the latter with the remaining part of the patch. Groove 11 also houses a small radial positioning rib 13, which allows module 1 to be fitted in one way only onto the remaining part of the patch. This module 1 is also provided with a small gripping lug 16, intended to facilitate its installation and especially its removal when it has to be replaced. This module 1 comprises the first disposable element when the quantity of drug in the reservoir is used up. This module 1 may evidently be formed by giving the electrodes any other form known by the prior art. As such, module 1 does not form part of the invention; it forms part of the invention only to the extent that it co-operates with the two other modules.

Power module 2, realized in a rigid plastic material, is formed to receive a power supply 20 necessary for an administration of drugs by electrophoresis or iontophoresis and also comprises, on the one hand mechanical assembly means 21, 22a, 22b and electrical connection means 23a, 23b, 24, 25 with active module 1 and electronic module 3, and on the other hand attaching means 26a, 26b to the body of a patient.

Figure 4:
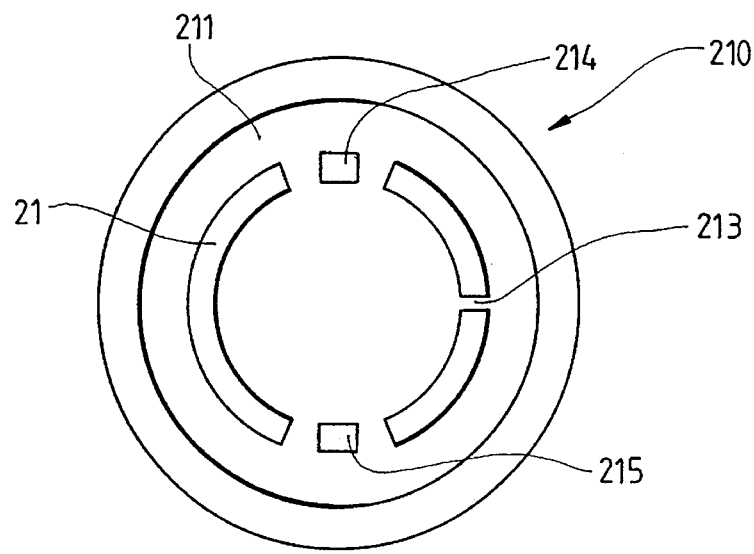
FIG. 4 shows a bottom view of the power module plate.
Figure 5:
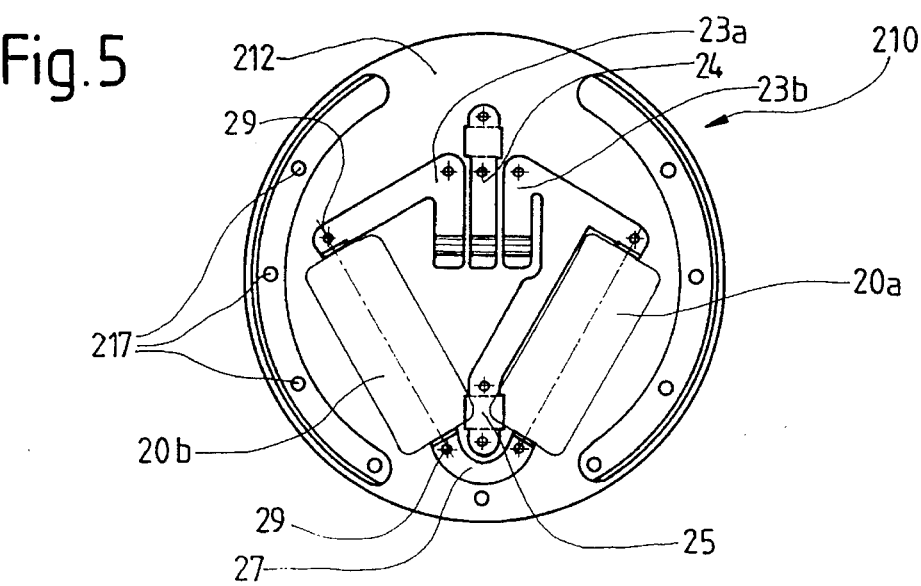
FIG. 5 shows a top view of the power module cover.
Figure 6:
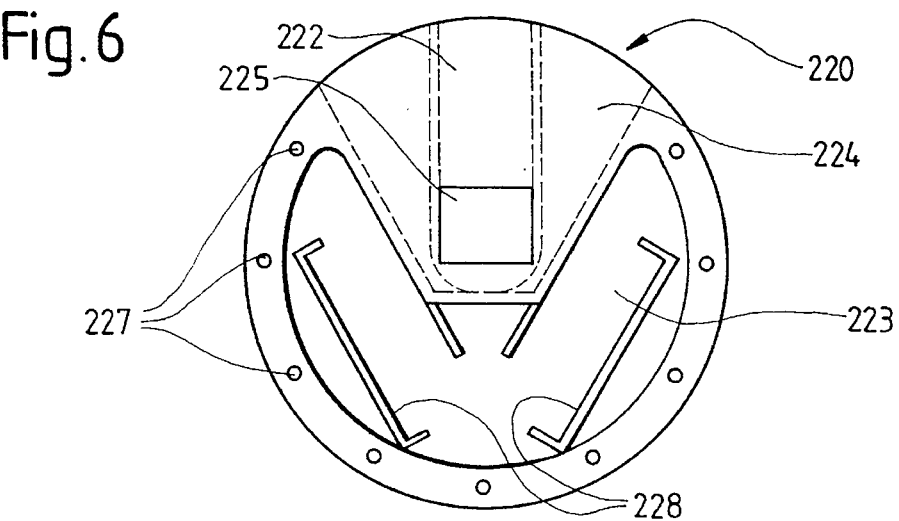
FIG. 6 shows a bottom view of the power module cover.

Referring now to FIGS. 4, 5 and 6, it will be noted that the assembly and the connections with active module 1 are achieved by means situated on the lower part of module 2, and the assembly and connections with electronic module 3 are achieved by means situated on its upper part. To this end, module 2 is formed of two parts, obtained for example by molding or by thermoforming a plastic material, to form a plate 210 whose external face 211 is oriented towards active module 1 and a cover 220 whose external part 221 is intended to support electronic module 3. Plate 210 and cover 220 are joined together by their opposite faces 212, 222 holding in place means for fixing 26a, 26b to the body of a patient. In the patch as shown in FIGS. 1 to 6, attachment means 26a, 26b are formed by two strips of elastic fabric able to be joined at their ends by a velcro ®-type fastening to hold the patch around a limb of a patient. Strips 26a, 26b are made to from one piece with module 2 by assemblage with cover 220 which is provided at its periphery with small lugs 227 locking into corresponding notches 217 of plate 210. The assemblage of plate 210 and cover 220 may also be achieved by any other appropriate non-detachable means, such as adhesive bonding or welding of the two parts.

Referring to FIGS. 4 and 5, showing respectively external faces 211 and 212 of plate 210, it will be noted that external face 211 comprises a discontinuous raised ring 21 which co-operates with groove 11 of active module 1 to hold the latter mechanically in place. Two discontinuities of ring 21 are occupied by contacts 214, 215, situated facing contacts 14, 15 of active module 1.

A third discontinuity 213 of ring 210 is intended to co-operate with positioning rib 13 of module 1.

Internal face 212 of plate 21-0 is structured to receive or to hold in place the connections and interconnections 23a, 23b, 24, 25 between power supply 20 and the two other modules. According to the embodiment shown, power supply 20 is formed by two rod-shaped batteries 20a, 20b (for example of type $R_1$), placed flat in a V shape, and connected in series by a connection 27. Connections 23a, 23b enable the two poles of power supply 20 to be connected to the electronic module. Connection 24 is formed to connect via a through hole across the plate, a terminal of the power supply to an electrode of active module 1 by the intermediary of contact 215. Interconnection 24 is formed to connect, via a through hole across plate 210, the second electrode of module 1 by the intermediary of contact 214, and an outlet terminal 34 of electronic module 3. The electrical connections and interconnections are achieved by known means, for example by cutting out a metallic sheet and positioning on the plate by fusion of the end of small positioning lugs 29.

Referring now to FIGS. 3 to 6 it will be noted that the second constitutive element of power module 2 is formed by a cover 220 of which a part of the internal face 222 is open to form a casing 223 intended to receive power supply 20, the other part being closed by a sheet 224 in which is arranged an aperture 225 giving access to the ends of connections 23a, 23b, 24 forming contact with electronic module 3. According to the embodiment shown, in which power supply 20 consists of two rod-shaped batteries placed flat on the plate, casing 223 has the general form of empty V shape, the supplemental ribs 228 being able to be provided to keep the batteries in place.

On external part 221 of cover 220, the external walls of casing 223 and the external face of sheet 224 delimit a casing 226 having the general form of a circular sector, intended to receive electronic module 3. In the embodiment shown, the guiding of electronic module 3 into casing 226 and its holding in place are ensured by rails 22a, 22b in dovetail co-operating with the corresponding spigot part 31 situated on the internal face of electronic module 3. This guiding and fixing of electronic module 3 onto power module 2 may evidently, without departing from the scope of the invention, be achieved by any other appropriate means enabling electronic module 3 to be installed and removed easily and quickly. It is for example possible to place the rails and ribs onto the faces facing electronic module 3 and cover 220.

In the embodiment shown, electronic module 3 has the form of a small case whose contour is complementary to that of casing 226 of power module 2. It includes in its interior an electronic circuit 30, known per se for managing all the usual parameters of a treatment by electrophoresis or iontophoresis, as a function of the drug to be administered and the patient to be treated. These different parameters may be initialized in circuit 30 by means of control buttons 37, 38 and visualized on a display screen 36, these elements being situated on the external face of the case. On its internal face, the case comprises contacts 33a, 33b, 34, facing the contacts situated on connections 23a, 23b and 24 of power module 2. The electronic module may possess its own power supply, for example a small long life button-shaped battery. It may also possess a circuit 30 provided with a non-volatile memory and have as its only power supply that of power module 2 when the electronic module is in place. As such, module 2 does not form part of the invention; it forms part of the invention only to the extent that it cooperates with the two other modules.

FIG. 7 shows another embodiment of a patch according to the invention, in which the replacement of the two rod-shaped batteries by two button-shaped batteries (for example of type DA630H) results in a modification of the geometrical shape of said patch, whilst utilizing the same principles of mechanical and electrical connection of the three modules, of which only electronic module 3 is re-usable. According to this embodiment, the patch has a general oval form. Active module 1 assumes this form by supporting, on all or part of its external surface, at least one system of electrodes and one drug reservoir. Power module 2, still comprising a plate and a cover, supports a button-shaped battery at each of its ends, casing 226 reserved to electronic module 3 which here has a central position, display screen 36 being situated in the center and control buttons 37, 38 on either side of said screen 36, on extensions of the case of module 3, above cover 220 of module 2. Attachment to the body of a patient is ensured by means of an adhesive ring 26 held in place between plate 210 and cover 220.

The present invention, which has just been illustrated by two examples to facilitate comprehension, is evidently not limited to these two embodiments. Without departing from the scope of the present invention, a man skilled in the art is capable of effecting appropriate changes to the form, methods of mechanical and electrical or other assembly, insofar as the power module constitutes the principal part of the patch according to the invention.

What is claimed is:

1. A device for ambulatory treatment by transdermic administration of drugs by electrophoresis or iontophoresis, said device comprising an assembly of three detachable modules including a first active module having at least one system of electrodes and one drug reservoir, a second power module having a power supply and a third electronic module having an electronic circuit and a display screen, wherein when the three modules are assembled together the power module is situated between the first and third modules, said power module power supply including one or more batteries and said power module having mechanical assembly means and electrical contacts, said mechanical assembly means interlocking with corresponding mechanical assembly means on the first and third modules and said electrical contacts contact contacts provided on the first and third modules to detachably mechanically and electrically interconnect the power module to the first and third modules whereby said first and third modules may be individually detached and reattached to said power module, and attachment means for attaching the device to the body of a patient.

2. A device according to claim 1, wherein said power module is formed by the assembly of a plate having an external face and an internal face and a cover having an external part and an internal part the external face of said plate being oriented towards the active module, the external part of said cover being designed for supporting the electronic module, and the internal face of said plate being joined to the internal part of said cover and fitting at least a portion of the means for attaching the device to the body of a patient.

3. A device according to claim 2, wherein the external face of the plate includes a portion of said power module mechanical assembly means comprising a ring for fixing the active module, said ring being provided with discontinuities, and two electrical contacts for separately connecting the power supply and the electronic module, said contacts facing corresponding contacts of the active module.

4. A device according to claim 3, wherein one of the discontinuities of the ring enables the active module to be positioned in a single way relative to the power module.

5. A device according to claim 2, wherein the internal face of the plate is structured to secure the contacts between the power supply and separately the active module and the electronic module.

6. A device according to claim 2, wherein one part of the internal face of the cover forms a casing structured to receive the power supply, and another part of the cover is closed by a sheet which houses an aperture for the contacts.

7. A device according to claim 6, wherein the power supply is formed by two rod-shaped batteries in series, placed flat in a V shape on the internal face of the plate, the sheet occupying the interior of the V.

8. A device according to claim 6, wherein the power supply is formed by two button-shaped batteries placed flat on the internal face of the plate, the sheet being positioned between said button-shaped batteries.

9. A device according to claim 6, wherein the casing is delimited by the external walls of the casing of the power supply and by the external face of the sheet, and is provided with mechanical assembly means for holding the electronic module.

10. A device according to claim 6 wherein the power supply comprises two batteries having a shape selected from the group of battery shapes consisting of rod-shaped and button-shaped.

11. A device according to claim 9, wherein the mechanical assembly means are formed by a dovetail cut arranged in the sheet.

12. A device according to claim 9, wherein the mechanical assembly means comprise elements selected from the group of elements consisting of rails and ribs placed on the walls of the casing.

13. A device according to claim 2, wherein the attachment means comprise strips of elastic fabric provided at their end with velcro ®-type fastenings, said strips being gripped between the plate and the cover.

14. A device according to claim 2, wherein the attachment means are formed by adhesive strips encircling at least a part of the power module, said strips being gripped between the plate and the cover.

15. A device according to claim 2, wherein the plate and the cover comprise a material selected from the group of materials consisting of moldable or thermo formable plastic material.

16. A device according to claim 2 wherein the attachment means comprises means selected from the group of attachment means consisting of strips of elastic fabric provided with velcro ®-type fastenings and adhesive strips.

* * * * *